United States Patent [19]

Layton et al.

[11] 4,384,485

[45] May 24, 1983

[54] DEVICE FOR INDICATING LIQUID LEVEL

[75] Inventors: Terry N. Layton, Arlington Heights, Ill.; Jack D. Merry, Summerville, S.C.; Frank N. Miller, Racine, Wis.

[73] Assignee: The Kendall Company, Boston, Mass.

[21] Appl. No.: 120,699

[22] Filed: Feb. 11, 1980

[51] Int. Cl.³ .............................................. G01F 1/00
[52] U.S. Cl. ..................................... 73/215; 116/334; 128/771
[58] Field of Search .............. 73/215, 216, 863.52; 116/206, 334; 422/56, 57; 128/771

[56] References Cited

U.S. PATENT DOCUMENTS

| 2,004,502 | 6/1935 | Fieberling | 116/27 |
|---|---|---|---|
| 2,214,354 | 9/1940 | Snelling | 116/204 |
| 2,249,867 | 7/1941 | Snelling | 116/207 X |
| 2,787,238 | 4/1957 | Luce | 116/206 |
| 3,093,242 | 6/1963 | Huyck et al. | 116/206 X |
| 3,466,145 | 9/1969 | Van Duyne | 73/863.52 |
| 3,523,011 | 8/1970 | Bhiwandker et al. | 422/57 |
| 3,620,676 | 11/1971 | Davis | 116/200 X |
| 3,774,455 | 11/1973 | Seidler et al. | 128/771 X |
| 3,871,230 | 3/1973 | Dye et al. | 73/215 |
| 3,884,072 | 5/1975 | Cheng | 73/215 |
| 4,179,397 | 12/1979 | Rohowetz | 116/206 |
| 4,216,245 | 8/1980 | Johnson | 422/57 X |

Primary Examiner—Daniel M. Yasich

[57] ABSTRACT

In a device for measuring the approximate peak flow rate of a liquid discharge, the improvement comprising an indicating element bearing water-soluble ink.

3 Claims, 8 Drawing Figures

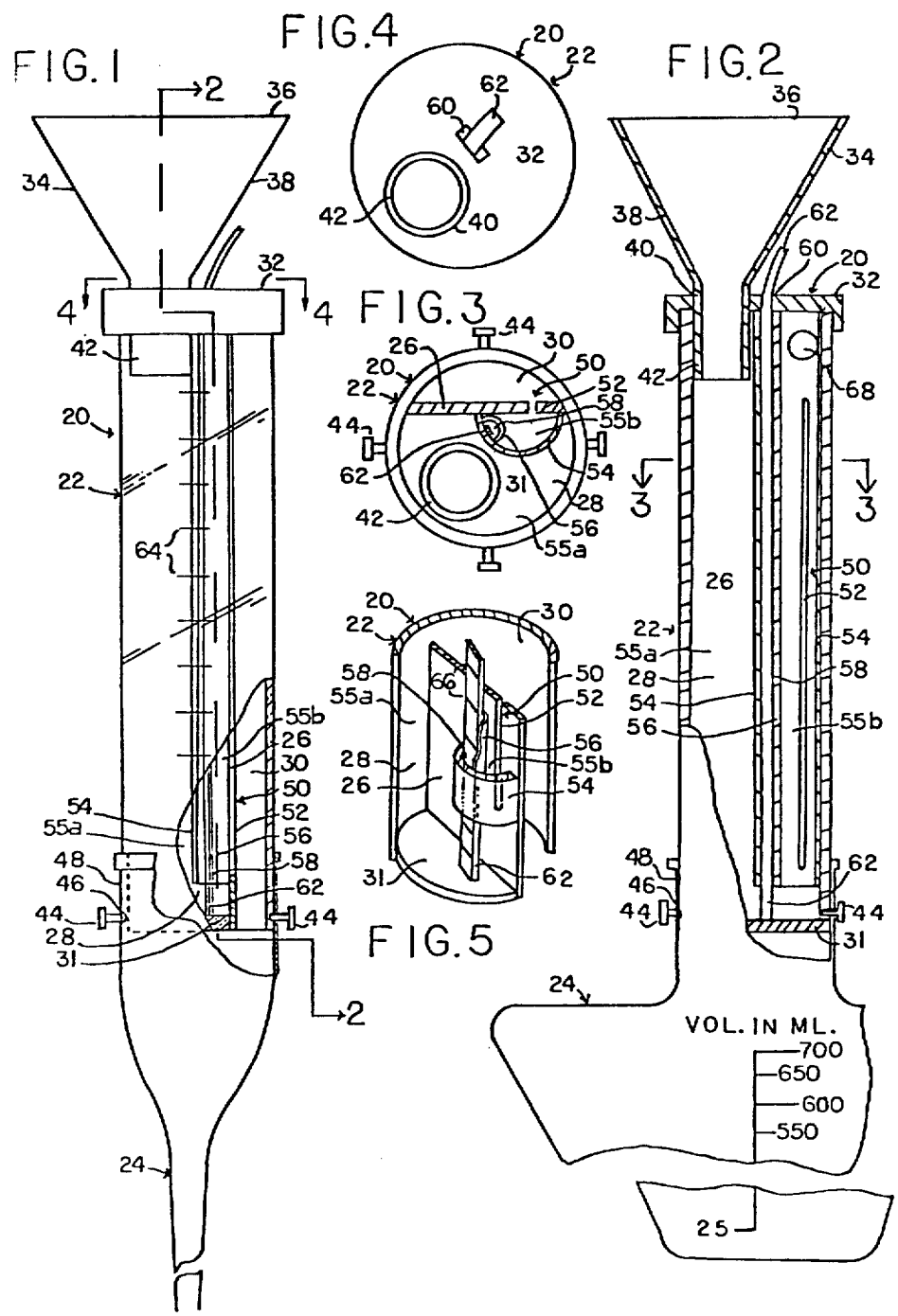

DEVICE FOR INDICATING LIQUID LEVEL

This invention relates to a liquid indicating strip for use in combination with a device for measuring the approximate peak flow rate of a liquid discharge.

Paper indicators impregnated with chemicals designed to permit screening for abnormalities in urine have long been know. Thus, it is conventional to detect albumin, protein, glucose, bilirubin, ketone bodies, hemoglobin, phenylpyruvic acid, etc. by immersing an appropriate indicator strip in a urine sample.

There also exist several devices for measuring the approximate peak flow rate of a liquid discharge, and which may be self-administered by a patient. Such devices are described in Dye et al. U.S. Pat. No. 3,871,230 and Ciarico U.S. Pat. No. 3,871,231. The descriptions of U.S. Pat. Nos. 3,871,230 and 3,871,231 are hereby incorporated by reference.

An indicating strip for use in conjunction with the above devices has been described in Cheng U.S. Pat. No. 3,884,072. The strip employs an indicator substance which, when exposed to urine, changes color as a result of a chemical change. However, a problem associated with such chemical detection strips is that the chemical indicator substances can deteriorate during storage, particularly under conditions of high temperature or humidity. Further, after use, the maximum flow line can lose its clarity during storage, particularly under adverse conditions.

Now it has been found in accordance with the present invention that data on aqueous liquids such as urine can be readily obtained by employing an indicator which bears watersoluble ink in conjunction with an apparatus for measuring the approximate peak flow rate of a liquid discharge.

The invention will be better understood by reference to the following description thereof, in which the apparatus is as described in aforementioned U.S. Pat. No. 3,871,230 and the accompanying drawings in which:

FIG. 1 is a fragmentary elevational view, partly broken away, of the flow measuring apparatus of the present invention;

FIG. 2 is a fragmentary elevational view, partly broken away, and taken partly in section substantially as indicated along the line 2—2 of FIG. 1;

FIG. 3 is a sectional view taken substantially as indicated along the line 3—3 of FIG. 2;

FIG. 4 is a sectional view taken substantially as indicated along the line 4—4 of FIG. 1; and FIG. 5 is a fragmentary perspective view of the lower internal structure of the flow measuring apparatus showing the lower portion of an upright wall, shield, flange, and indicating strip.

Figure 6:
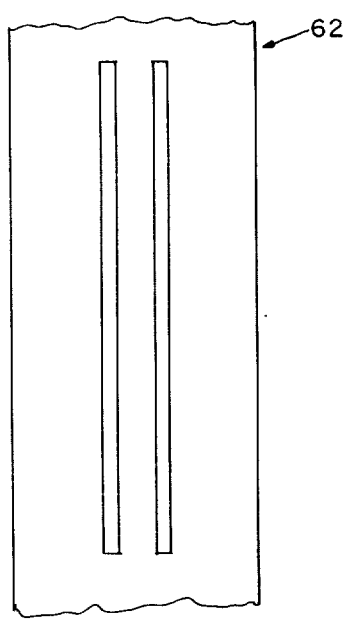
FIG. 6 shows one preferred pattern of water-soluble ink on the water-absorptive indicator element of the present invention.

Referring now to FIGS. 1 and 2, there is shown an apparatus, generally designated 20, for measuring a discharge of liquid. The apparatus 20 includes a hollow receptacle designated generally 22 and a container or bag designated generally 24 removably secured to the receptacle 22. However, if desired, the container 24 may be made integral with the receptacle at its lower end. Preferably, the receptacle and container are made from a suitable transparent material, such as plastic.

As illustrated in FIGS. 1-3, and 5, the receptacle 22, which is preferably cylindrically shaped, has an upright wall 26 which extends laterally across the inside of the receptacle and which extends vertically the height of the receptacle. The upright wall 26 separates the inside of the receptacle 22 into a compartment 28 and a channel 30. The lower end of the compartment 28 is closed by a bottom wall 31, while a cap 32 covers the upper end of the receptacle 22. If desired, the cap 32 may be removably secured to the upper end of the receptacle to provide access to the inside of the receptacle.

As shown in FIGS. 1, 2, and 4, the receptacle 22 has a funnel-shaped member 34 adjacent its upper end which defines an inlet port 36 to receive a liquid discharge, and which has a tapered portion 38 and a lower depending portion 42 to direct the discharge into the inside of the receptacle. The cap 32 has an aperture 40 to removably receive the lower depending portion 42 of the funnel-shaped member 34. The positional relationship of the funnel-shaped member 34 to the inside of the receptacle 22 is best shown in FIG. 3, where the lower depending portion 42 of the funnel-shaped member 34 is shown in phantom lines. As shown, the compartment 28 of the receptacle 22 is positioned below the depending portion 42 and the inlet port 36, such that liquid passes through the funnel-shaped member 34 into the compartment 28.

As shown in FIGS. 1-3, the receptacle 22 has a plurality of outwardly projecting bosses 44, and the container 24 has a plurality of corresponding apertures 46 in the sides of an upper tubular section 48 of the container 24. Thus, the lower end of the receptacle 22 may be inserted into the upper tubular section 48 of the container 24, and the bosses 44 are received in the apertures 46 to removably secure the container 24 to the lower end of the receptacle 22.

As illustrated in FIGS. 1-3, and 5, the upright wall 26 has opening means, generally designated 50, which preferably comprises a vertical slot 52 having parallel sides, communicating between the compartment 28 and the channel 30. Preferably, the slot 52 or opening means is spaced slightly from the lower end of the receptacle 22, as shown.

A shield 54 if secured to the upright wall 26 in the compartment 28. The shield 54 is spaced from and covers the slot 52, in order to prevent liquid which enters the compartment from splashing against the slot 52. The shield 54 is spaced from the lower end of the receptacle 22 or the bottom wall 31 to permit passage of liquid under the lower end of the shield 54 to the slot 52. The shield 54 extends vertically in the compartment 28 at least coextensive with the vertical length of the slot 52. However, the shield 54 preferably extends to the upper end of the upright wall 26 or compartment 28 to prevent the inadvertent passage of liquid over the top of the shield 54. Although, for convenience, the shield 54 is shown as a semi-cylinder, it is understood that the shield 54 may have any suitable shape which prevents splashing of incoming liquid against the slot 52, and the shield 54 may be secured to the side walls of the receptacle 22, rather than the upright wall 26 itself, if desired.

As shown, the shield 54 separates the compartment 28 into a first chamber 55$a$ positioned to receive the discharge passing through the inlet port 36 and into a second chamber 55$b$ which communicates with the first chamber 55$a$ adjacent its lower end. It is readily apparent that the chambers 55$a$ and $b$ may be formed individually, such that they are separated by means other than a wall, i.e., other than the shield shown in the drawings, with a passageway communicating between the two chambers adjacent their lower ends. For example, the chambers 55a and b may be defined by separate tubes which are connected by a passageway adjacent their lower ends.

A flange 56 is secured to the shield 54 intermediate the shield 54 and the upright wall 26. The flange 56 is spaced from the lower end of the receptacle 22 or the bottom wall 31, and defines, with the shield 54, a vertical passageway 58. Preferably, the flange 56, as well as the shield 54, extends to the upper end of the receptacle, to prevent incoming liquid from entering the upper end of the passageway 58, whereas liquid is free to enter the passageway 58 through its lower end, since both the shield 54 and flange 56 are spaced from the lower end of the receptacle 22 in the compartment 28.

As shown in FIGS. 2 and 4, the cap 32 has an aperture 60 positioned above the upper end of the passageway 58 for insertion of an indicating strip 62 through the aperture 60 and into the passageway 58 from above.

As illustrated in FIGS. 1-3, and 5, the indicating strip 62 is pushed downwardly through the passageway 58 until the bottom of the strip 62 is positioned adjacent the lower end of the receptacle 22, and the strip 62 preferably has a length corresponding to at least the height of the receptacle to facilitate insertion and removal of the strip.

The carrier material for the indicating strip 62 of the present invention may be any absorptive or non-absorptive material which can bear water-soluble ink. Strip 62 is mounted in the device so as to extend both above and below the expected level of the liquid in compartment 28, and carries or bears a water-soluble ink extending both above and below the expected liquid level. The water-soluble ink may cover the entire strip 62 or it may be confined to one or more restricted zones, e.g., a band or bands, or row or other array of dots or dashes or other symbols or designs, extending across the expected liquid level. When a non-absorptive carrier is used, the liquid to be measured, which has been collected in the compartment 28, dissolves that portion of the water-soluble ink zone with which it comes in contact, which is then dispersed throughout the liquid. The solubilization and dispersal of the ink produces a visible line on the carrier, below which the ink has largely been removed. When an absorptive carrier is used, the ink is preferably applied in such a way that areas of the carrier remain unprinted, in contrast to the zone bearing the water-soluble ink. The liquid to be measured, which has been collected in compartment 28, dissolves the ink, which then spreads a limited distance into adjacent unprinted areas, so that there is produced a visible line below which the ink has to some degree dispersed across the carrier surface.

The strip 62 may be replaced after use of the apparatus, thus rendering the apparatus for further use, if desired.

In operation, the receptacle is positioned to receive a discharge of aqueous liquid, such as a urine stream during voiding, through the inlet port 36. As the liquid discharge passes into the receptacle through the inlet port 36, the tapered portion 38 and depending portion 42 direct the discharge into the compartment 28. As the discharge continues, the liquid collects in the lower part of the compartment 28 until it reaches the height of the lower end of the slot 52, and once the height of the liquid in the compartment 28 further rises, the liquid begins to pass through the lower end of the slot 52 into the channel 30. The liquid then drains through the lower end of the channel 30 into the container 24 for collection.

For a given rate of flow of the discharge into the receptacle the liquid attains a fixed height in the compartment 28, and the liquid passes at a fixed rate of flow through the slot 52. Hence, if the rate of flow of the liquid discharge into the receptacle increases, the height of liquid in the compartment raises an additional amount, and the rate of flow through the slot 52 also increases, since the liquid flows through a larger vertical portion of the slot 52. Thus, as long as the rate of flow of the discharge into the receptacle increases, the height of liquid in the compartment 28 continues to raise, and the rate of flow of liquid through the slot 52 also increases. When the flow rate of the incoming discharge abates, the liquid drains from the compartment 28 into the channel 30 faster than it enters the compartment, and the height of the liquid in the compartment begins to subside.

Peak flow rate of the incoming liquid discharge may be defined as the maximum rate of flow of the discharge. Since the height of liquid in the compartment raises or lowers responsive to an increase or decrease, respectively, of the flow rate of the incoming discharge, it is apparent that the maximum height of liquid attained in the compartment during the discharge serves as an indication of the approximate peak flow rate of the discharge. Although anomalies in the discharge, such as a momentary surge of the discharge, may not be ultimately reflected in the maximum liquid height in the compartment, due, in part to the lag between the time the discharge enters the receptacle and the time it enters the compartment, the apparatus determines the peak flow rate with sufficient accuracy for such purposes as are under discussion. In particular, a urine stream during voiding has a relatively slow rate of change of flow rate, and apparatus of the present invention indicates a peak flow rate for the discharge which is sufficiently accurate for purposes of diagnosing a patient.

Accordingly, the indicating means, comprising a wall portion defined by the shield 54 and flange 56 and the indicating strip 62, has been provided to automatically record the approximate maximum height of liquid collected in the compartment 28 during the liquid discharge. Since liquid in the compartment 28 passes into the lower end of the passageway 58, the maximum liquid height attained in the compartment 28 during the liquid discharge is also proportionately reached in the passageway 58, which is indicated by a color contrast on the indicating strip 62. After the liquid discharge has been completed, a direct reading of the approximate peak flow rate may be determined by indicia 64 on the receptacle, as shown in FIG. 1, or by indicia 66 on the indicating strip 62 itself, as shown in FIG. 5.

In the event that the rate of flow of the incoming discharge is sufficiently abnormal, such that its flow rate greatly exceeds the value which has been expected, an enlarged opening 68 is provided in the upright wall 26 adjacent its upper end for rapid passage of liquid from the compartment 28 into the channel 30. Thus, overflow of the liquid out of the receptacle is prevented. The indicating strip 62 will provide an indication that the incoming discharge is abnormally high and that an overflow condition has occurred, since the indicating strip will change color contrast to a vertical height corresponding to the opening 68.

The ink employed in accordance with the present invention can comprise any water-soluble ink such as the inks employed in many readily available writing pens.

The non-absorptive carrier employed in accordance with the present invention can be any non-absorptive material to which water-soluble ink will adhere and from which water-soluble ink will be removed upon contact with an aqueous liquid. Preferably, the non-absorptive carrier has been calibrated to allow the reading of the maximum height of a liquid which has been collected in the compartment 28 of the liquid peak flow rate measuring device.

Figure 7:
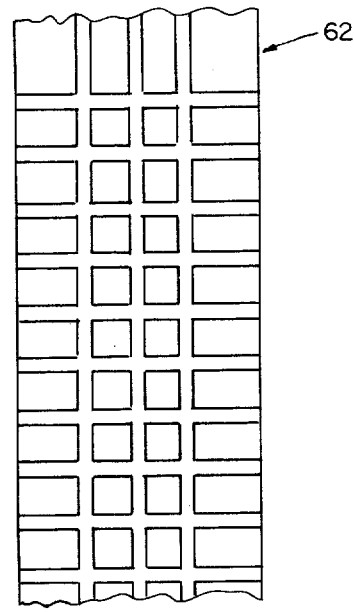
FIG. 7 shows a cross hatched pattern.
Figure 8:
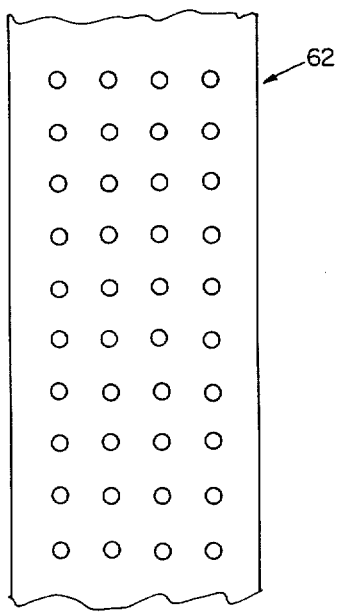
FIG. 8 shows a dotted pattern.

The absorptive carrier employed in accordance with the present invention can be any absorptive material such as paper or fabric which will bear water-soluble ink. Preferably, it comprises a strip of material having limited absorbency such as bond paper which has been calibrated to allow the reading of the maximum height of a liquid which has been collected in compartment 28 of the liquid peak flow rate measuring device. The ink is printed onto the carrier in any pattern which leaves unprinted areas on the carrier. A preferred pattern, shown in FIG. 6, is a pair of bands parallel with the longitudinal axis of the carrier. The bands are preferably approximately 0.020 inches wide and 0.062 inches apart. Other preferred patterns are cross hatched patterns, shown in FIG. 7, and dots arranged, as shown in FIG. 8, in several rows (e.g., 3 to 5) which are parallel to the longitudinal axis of the carrier. For all patterns, the ink extends both above and below the expected level of the liquid in compartment 28.

The indicating strip of the present invention exhibits excellent storage capability, even under conditions of high temperature and humidity. In addition, the maximum line does not tend to creep up or become indistinct during storage so an accurate permanent record can be maintained.

What is claimed is:

1. A device for measuring the approximate peak flow rate of a urine discharge, comprising: a receptacle having an inlet port adjacent the upper end of the receptacle to receive a urine discharge; a compartment in the receptacle below the inlet port to receive the discharge passing through the inlet port; a channel adjacent the compartment; wall means separating the compartment from the channel; opening means communicating between the compartment and the channel for permitting passage of the urine discharge from the compartment to the channel as the discharge collects in the compartment; a generally vertically disposed element for indicating the level of liquid present in the compartment, the element extending through a predetermined range of expected liquid levels within the compartment, the element having a first portion located below the lowest, predetermined, expected liquid level in said compartment, a second portion located above the highest, predetermined, expected liquid level in the compartment, and a third portion located between said first and second portions; and visible water-soluble ink indicia carried by said element in each said portion, said element and ink being substantially inert to conditions of high temperature and humidity, said ink indicia being present in at least two bands parallel to the longitudinal axis of said element, the ink in said portions, when in contact with an aqueous liquid, solubilizing and dispersing in the aqueous liquid and across the element, whereby said ink is extracted from said element, into said liquid and redeposited onto said element, said ink further being diffused on said element and spread thereacross, thereby to provide a permanent, visible change in the appearance of the immersed portion of said element in contrast to the appearance of the unimmersed portion of said element and create a visible line of demarcation on said element between the immersed and unimmersed portion of said element, said unimmersed portion of said element remaining unchanged, thus to clearly, visibly and permanently indicate the level of liquid in the compartment during presence of the liquid in the compartment and after the liquid has been drained from the compartment.

2. A device for measuring the approximate peak flow rate of a urine discharge, comprising: a receptacle having an inlet port adjacent the upper end of the receptacle to receive a urine discharge; a compartment in the receptacle below the inlet port to receive the discharge passing through the inlet port; a channel adjacent the compartment; wall means separating the compartment from the channel; opening means communicating between the compartment and the channel for permitting passage of the urine discharge from the compartment to the channel as the discharge collects in the compartment; a generally vertically disposed element for indicating the level of liquid present in the compartment, the element extending through a predetermined range of expected liquid levels within the compartment, the element having a first portion located below the lowest, predetermined, expected liquid level in said compartment, a second portion located above the highest, predetermined, expected liquid level in the compartment, and a third portion located between said first and second portions; and visible water-soluble ink indicia carried by said element in each said portion, said element and ink being substantially inert to conditions of high temperature and humidity, said ink indicia being present in at least three rows of dots, said rows being parallel to the longitudinal axis of said element, the ink in said portions, when in contact with an aqueous liquid, solubilizing and dispersing in the aqueous liquid and across the element, whereby said ink is extracted from said element, into said liquid and redeposited onto said element, said ink further being diffused on said element and spread thereacross, thereby to provide a permanent, visible change in the appearance of the unimmersed portion of said element and create a visible line of demarcation on said element between the immersed and unimmersed portion of said element, said unimmersed portion of said element remaining unchanged, thus to clearly, visibly and permanently indicate the level of liquid in the compartment during presence of the liquid in the compartment and after the liquid has been drained from the compartment.

3. A device for measuring the approximate peak flow rate of a urine discharge, comprising: a receptacle having an inlet port adjacent the upper end of the receptacle to receive a urine discharge; a compartment in the receptacle below the inlet port to receive the discharge passing through the inlet port; a channel adjacent the compartment; wall means separating the compartment from the channel; opening means communicating between the compartment and the channel for permitting passage of the urine discharge from the compartment to the channel as the discharge collects in the compartment; a generally vertically disposed element for indicating the level of liquid present in the compartment, the element extending through a predetermined range of expected liquid levels within the compartment, the element having a first portion located below the lowest, predetermined, expected liquid level in said compartment, a second portion located above the highest, predetermined, expected liquid level in the compartment, and a third portion located between said first and second portions; and visible water-soluble ink indicia carried by said element in each said portion, said element and ink being substantially inert to conditions of high temperature and humidity, said ink indicia being present in a cross-hatched pattern, the ink in said portions, when in contact with an aqueous liquid, solubilizing and dispersing in the aqueous liquid and across the element, whereby said ink is extracted from said element, into said liquid and redeposited onto said element, said ink further being diffused on said element and spread thereacross, thereby to provide a permanent, visible change in the appearance of the immersed portion of said element in contrast to the appearance of the unimmersed portion of said element and create a visible line of demarcation on said element between the immersed and unimmersed portion of said element, said unimmersed portion of said element remaining unchanged, thus to clearly, visibly and permanently indicate the level of liquid in the compartment during presence of the liquid in the compartment and after the liquid has been drained from the compartment.

* * * * *